United States Patent [19]
Mathis et al.

[11] Patent Number: 5,846,256
[45] Date of Patent: Dec. 8, 1998

[54] DEVICE AND METHOD FOR INSERTING A BIOCOMPATIBLE MATERIAL INTO THE CORNEAL STROMA

[75] Inventors: Mark L. Mathis, Fremont; John A. Scholl, Danville; Robert A. Proudfoot, Santa Clara; Thomas A. Silvestrini, Alamo, all of Calif.

[73] Assignee: KeraVision, Inc., Fremont, Calif.

[21] Appl. No.: 462,297

[22] Filed: Jun. 5, 1995

Related U.S. Application Data

[62] Division of Ser. No. 178,577, Jan. 7, 1994.

[51] Int. Cl.⁶ .................................................... A61F 9/00
[52] U.S. Cl. ........................................... 606/166; 128/774
[58] Field of Search .................. 606/166, 170, 606/102, 172, 107; 128/774

[56] References Cited

U.S. PATENT DOCUMENTS

| | | |
|---|---|---|
| 2,249,906 | 7/1941 | Longoria . |
| 4,180,075 | 12/1979 | Marinoff ................................ 606/166 |
| 4,319,575 | 3/1982 | Bonte . |
| 4,423,728 | 1/1984 | Lieberman . |
| 4,429,696 | 2/1984 | Hanna . |
| 4,452,235 | 6/1984 | Reynolds . |
| 4,688,570 | 8/1987 | Kramer et al. . |
| 4,796,623 | 1/1989 | Krasner et al. . |
| 4,815,463 | 3/1989 | Hanna . |
| 4,941,093 | 7/1990 | Marshall et al. . |
| 4,950,272 | 8/1990 | Smirmaul ............................... 606/107 |
| 4,997,437 | 3/1991 | Grieshaber . |
| 5,011,498 | 4/1991 | Krumeich et al. . |
| 5,090,955 | 2/1992 | Simon . |
| 5,217,464 | 6/1993 | McDonald ............................... 606/107 |
| 5,261,923 | 11/1993 | Soares ................................... 606/166 |
| 5,283,063 | 2/1994 | Freeman ................................ 606/107 |
| 5,372,580 | 12/1994 | Simon et al. . |
| 5,405,384 | 4/1995 | Silvestrini . |

FOREIGN PATENT DOCUMENTS

| | | |
|---|---|---|
| WO 88/100096 | 12/1988 | WIPO . |
| WO 93/20763 | 10/1993 | WIPO . |

OTHER PUBLICATIONS

Hartmann Chr., et al., "Intrastromale Implantation Eines Justierbaren Kunststoffringes Zur Hornhautrefraktionsänderung", *KongreB der Deutschen Gesellschaft für Intraokularlinsen Implantation*, delivered by H. Freyler et al., Springer–Verlag, Wien, pp. 465–475. The corresponding English language translation of the article authored by Hartmann, Chr., et al., entitled Intrastromal implantation of an adjustable plastic ring to alter the corneal refraction *Congress for German Society for Intraocular Lens Implantation*, delivered by H. Freyler et al., (7 pages total), is also enclosed.

Simón, G., et al., "Long term in vivo topographic studies of gel injection adjustable keratoplasty (GIAK)" *Abstracts: The Association for Research in Vision and Opthalmology*, Annual Meeting Abstract Issue, Sarasota, Florida, USA, May 2–May 7, 1993, p. 1248, (abstract 2679–52).

Simón, G., et al., "Refractive remodeling of the cornea by intrastromal rings" *Abstracts: Eighth International Congress of Eye Research*, Proceedings of the International Society for Eye Research, San Francisco, California, USA, Sep. 4–8, 1988, vol. V, (abstract No. 47).

(List continued on next page.)

*Primary Examiner*—Michael Buiz
*Assistant Examiner*—Kevin Truong

[57] ABSTRACT

This invention is an improved method and kit for producing a desired channel or pathway in the interlamellar space in the corneal stroma for inserting a biocompatible material. The biocompatible polymer may be an intrastromal corneal ring (ICR). The method involves the use of clockwise and counter-clockwise dissectors, and optionally channel connectors and finish channel connectors. The kit contains clockwise and counter-clockwise dissectors and optionally channel connectors, finish channel connectors and probes.

5 Claims, 11 Drawing Sheets

OTHER PUBLICATIONS

Simón, G., et al., "Refractive remodeling of the cornea by intrastromal rings" *The Association for Research in Vision and Ophthalmology*, Annual Spring Meeting, Sarasota, Florida, USA, Apr. 30–May 5, 1989, p. 187, (abstract 43).

Blavatskaia, D.E.D., "The use of intralamellar homoplasty in order to reduce refraction of the eye" *Überstzt. Aus. Oftalmol. Zh.* (1966) 7:530–537 which was apparently translated to *Arch. Soc. Ophthmol. Optom.* (1988) 6:31–325.

English translation of Brazilian Patent Application No. BR 8705060 (Mar. 21, 1989).

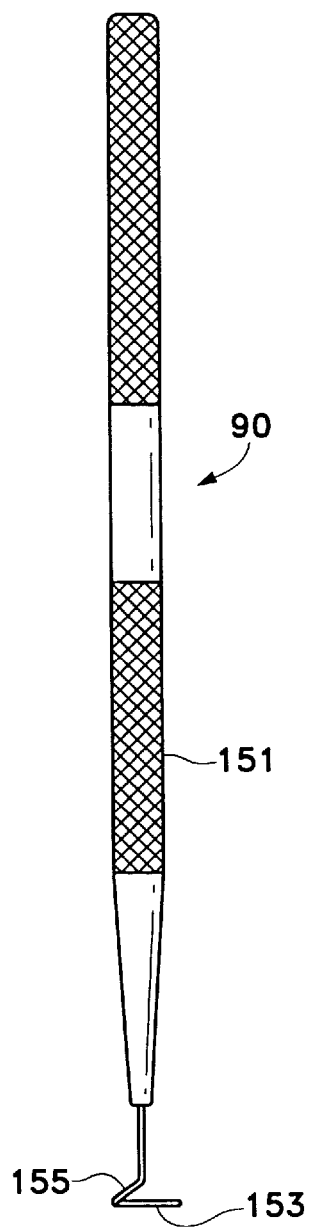
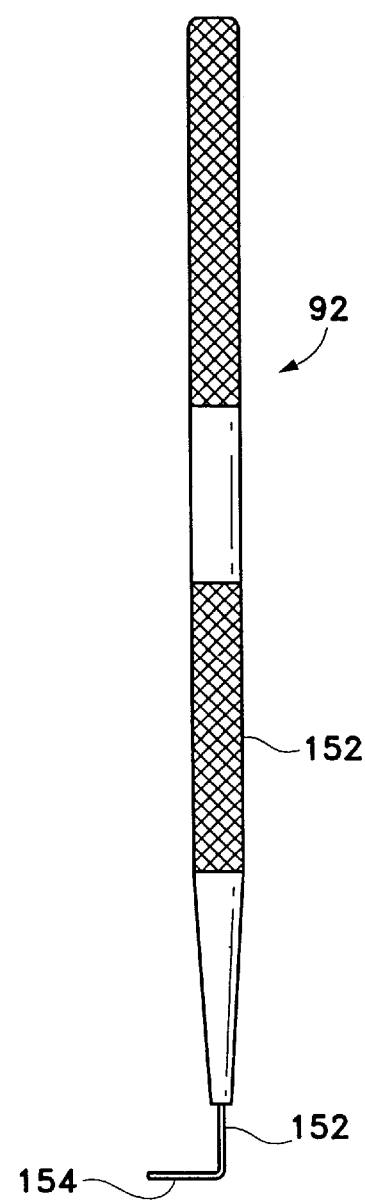
Fig. 15A
Fig. 16A
Fig. 15B
Fig. 16B

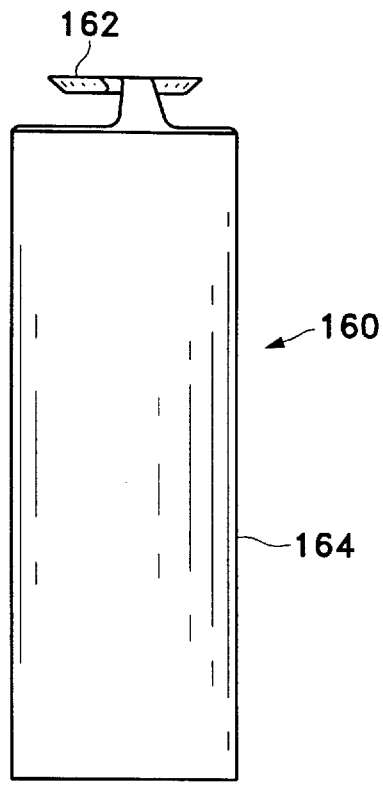
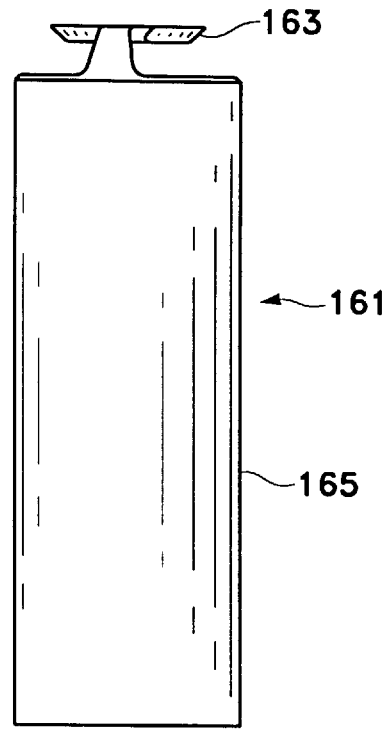
Fig. 17A            Fig. 18A
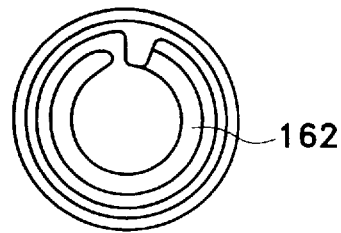
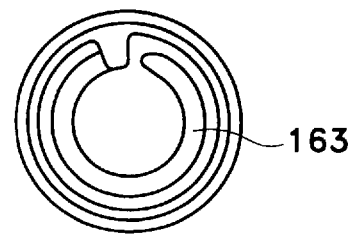
Fig. 17B            Fig. 18B 5,846,256

DEVICE AND METHOD FOR INSERTING A BIOCOMPATIBLE MATERIAL INTO THE CORNEAL STROMA

This application is a division of application Ser. No. 08/178,577 filed Jan. 7, 1994.

FIELD OF THE INVENTION

This invention is a surgical method and device for inserting a biocompatible material into an intrastromal passageway to permanently alter corneal curvature. The device and method allow for the placement of the material in the optimal position for maximal visual correction.

BACKGROUND OF THE INVENTION

Anomalies in the overall shape of the eye can cause visual disorders. Hyperopia ("farsightedness") occurs when the front-to-back distance in the eyeball is too small. In such a case, parallel rays originating greater than 20 feet from the eye focus behind the retina. In contrast, when the front-to-back distance of the eyeball is too large, myopia ("nearsightedness") occurs and the focus of parallel rays entering the eye occurs in from of the retina. Astigmatism is a condition which occurs when the parallel rays of light do not come to a single point within the eye, but rather have a variable focus due to the fact that the cornea is aspherical and refracts light in a different meridian at different distances. Some degree of astigmatism is normal, but where it is too high, it must often be corrected.

Hyperopia, myopia, and astigmatism are usually corrected by glasses or contact lenses. Surgical methods for the correction of such disorders are known. Such methods include radial keratotomy (see e.g., U.S. Pat. Nos. 4,815,463 and 4,688,570) and laser corneal ablation (see, e.g., U.S. Pat. No. 4,941,093).

Another method for correcting those disorders is through implantation of polymeric rings in the eye's corneal stroma to change the curvature of the cornea. Previous work involving the implantation of polymethylmethacrylate (PMMA) rings, allograft corneal tissue, and hydrogels is well documented. One of the devices involves a ring design that allows a split ring to be inserted into a channel dissected in the stromal layer of the cornea using a minimally invasive incision through which the channel for the implant is created and through which the implant is inserted.

U.S. Pat. No. 4,452,235 to Reynolds describes a method and apparatus for corneal curvature adjustment. The method involves inserting one end of a split end adjusting ring into the cornea of the eye and moving the ring in a circular path until its ends meet. The ends are thereafter adjusted relative to each other until the shape of the eye has assumed a desired curvature whereupon the ends are fixedly attached to maintain the desired curvature of the cornea.

PCT Application No. PCT/US93/03214 filed 7 Apr. 1993 describes a corneal vacuum centering guide and dissector for use in inserting an intrastromal corneal ring ("ICR"). The device is made of up of three major components: a vacuum centering guide, a barrel that fits within the inner bore of the centering guide and to which is attached the third major component, a circular dissecting ring. The three components are further described below.

The vacuum centering guide has a support base that has a proximal end, a distal end and a center section. The center section has a wall with a generally cylindrical bore with a central axis. The central section extends between the proximal and distal ends of the support base. The cylindrical bore has a ratio of length to diameter of between about 0.25:1 and 15:1. An annular vacuum chamber located at the proximal end of the support base is adapted to create an annular vacuum space when placed against the eye.

The barrel and dissector blade assembly is used in connection with the vacuum centering guide in order to produce the circular interlamellar pathway within the corneal stroma. The barrel fits within the inner bore of the centering guide. The dissecting ring is attached to the barrel in such a way that when an eye surgeon twists the barrel, the ring moves through the interlamellar space in the stroma producing the desired channel or pathway.

A drawback to prior methods to produce an intrastromal channel has been the inability to control the depth of the pathway since the dissector blade tended to create a non-planar channel. A new method for producing a more planar channel is described herein.

SUMMARY OF THE INVENTION

The present invention provides for an improved method and device for producing a desired channel or pathway in the interlamellar space in the corneal stroma for inserting a biocompatible material to permanently alter corneal curvature.

In one aspect, the invention is a method for making a channel in corneal tissue to facilitate inserting a biocompatible material into the corneal stroma of an eye. The method involves (a) cutting a small incision into the corneal stroma; (b) inserting a clockwise or counter-clockwise dissector blade into the incision and rotating it clockwise or counter-clockwise to produce a clockwise or counter-clockwise channel; (c) inserting the other of the clockwise or counter-clockwise dissector blades into the incision and rotating it clockwise or counter-clockwise to produce a clockwise or counter-clockwise channel; and optionally (d) inserting a clockwise probe into the clockwise channel and a counter-clockwise probe into the counterclockwise channel to see if the channels meet.

When the channels meet, the biocompatible material is inserted into the eye. When the channels do not meet, the method of the invention further involves (e) determining which of the clockwise or counterclockwise channels is the lower channel by overlaying the probe tips and observing the probes; (f) removing the probes; (g) inserting a clockwise or counter-clockwise channel connector into the lower channel depending on whether the lower channel is the clockwise or counter- clockwise channel and rotating it clockwise or counterclockwise or until the dissector is observed to break through into the upper channel; and (h) removing the dissector by rotating it in the opposite direction. If the breakthrough into the upper channel has occured, the biocompatible material is inserted into the eye.

If, however, the channels still do not meet, the method of the invention further involves: (i) inserting a clockwise or counter-clockwise finish channel connector into the lower channel depending on whether the lower channel is the clockwise or counter-clockwise channel and rotating it clockwise or counterclockwise until the channels meet or until the finish channel connecting instrument rotates around to the entry incision; and (j) removing the finish channel connector by rotating it in the opposite position. The biocompatible material is then inserted into the eye.

In another aspect, the invention is a kit useful for inserting an intrastromal corneal ring or other biocompatible material into the corneal stroma of an eye. The kit comprises: (a) a clockwise dissector; (b) a counter-clockwise dissector; (c) a clockwise channel connector; (d) a counter-clockwise channel connector; (e) a clockwise finish channel connector; (f) a counter-clockwise finish channel connector; (g) a clockwise probe; and (h) a counter-clockwise probe.

BRIEF DESCRIPTION OF THE DRAWINGS

FIG. 15A is a side view and FIG. 15B is a bottom view showing the clockwise probe.

FIG. 16A is a side view and FIG. 16B is a bottom view showing the counter-clockwise probe.

FIG. 17A is a side view and FIG. 17B is a top view showing the clockwise channel connector.

FIG. 18A is a side view and FIG. 18B is a top view showing the counter-clockwise channel connector.

DESCRIPTION OF THE INVENTION

Prior to explaining the details of the inventive method and devices, a short explanation of the physiology of the eye is needed to appreciate the functional relationship of the device to the eye.

Figure 1:
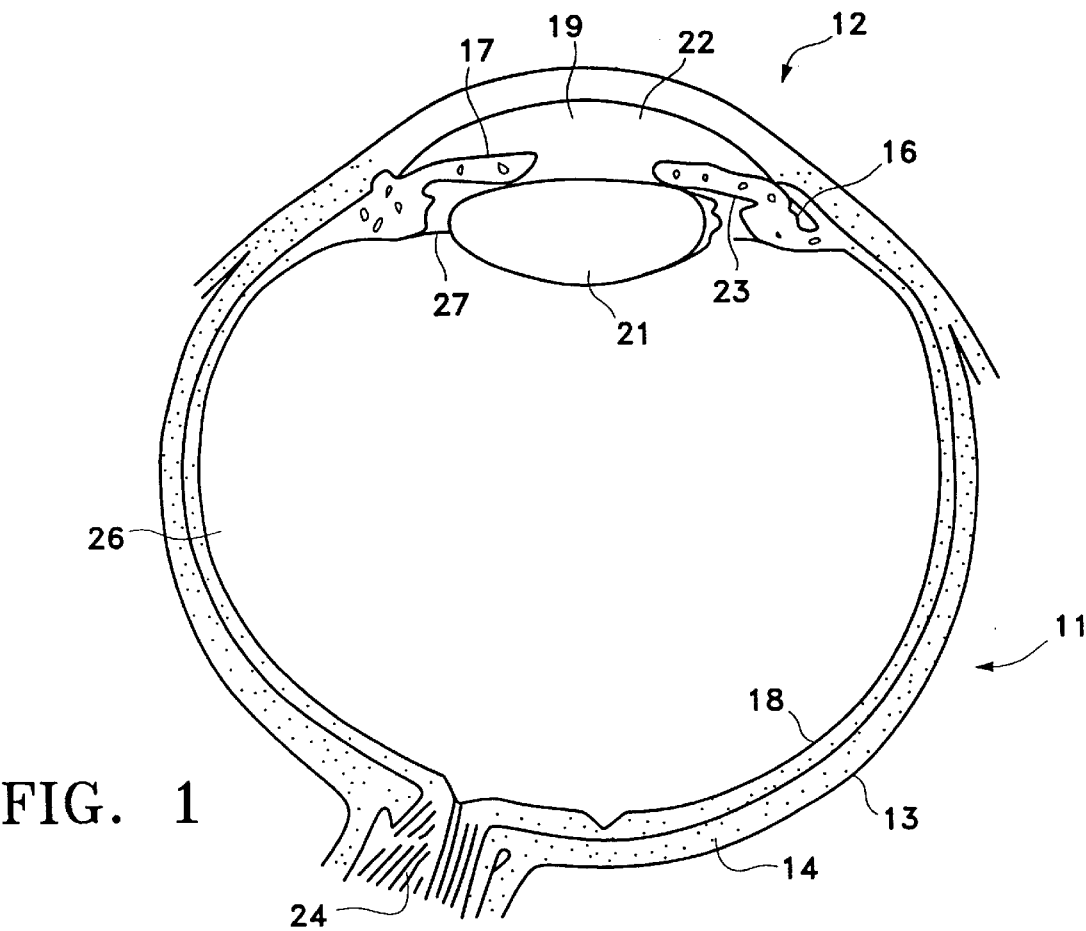
FIG. 1 is a drawing showing the horizontal section of an eye.

FIG. 1 show a horizontal section of the eye with the globe 11 of the eye resembling a sphere with an anterior bulged spherical portion representing the cornea 12.

The globe 11 of the eye consists of three concentric coverings enclosing the various transparent media through which the light must pass before reaching the sensitive retina 18. The outermost covering is a fibrous protective portion, the posterior five-sixths of which is white and opaque and called the sclera 13, and sometimes referred to as the white of the eye where visible to the front. The anterior one-sixth of this outer layer is the transparent cornea 12.

A middle covering is mainly vascular and nutritive in function and is comprised of the choroid 14, ciliary body 16 and iris 17. The choroid 14 generally functions to maintain the retina 18. The ciliary body 16 is involved in suspending the lens 21 and accommodation of the lens. The iris 17 is the most anterior portion of the middle covering of the eye and is arranged in a frontal plane. It is a thin circular disc corresponding to the diaphragm of a camera, and is perforated near its center by a circular aperture called the pupil 19. The size of the pupil varies to regulate the amount of light that reaches the retina 18. It contracts also to accommodation, which serves to sharpen the focus by diminishing spherical aberration. The iris 17 divides the space between the cornea 12 and the lens 21 into an anterior chamber 22 and posterior chamber 23. The innermost portion of covering is the retina 18, consisting of nerve elements which form the true receptive portion for visual impressions.

The retina 18 is a part of the brain arising as an outgrowth from the fore-brain, with the optic nerve 24 serving as a fiber tract connecting the retina part of the brain with the fore-brain. A layer of rods and cones, lying just beneath a pigmented epithelium on the anterior wall of the retina serve as visual cells or photoreceptors which transform physical energy (light) into nerve impulses.

The vitreous body 26 is a transparent gelatinous mass which fills the posterior four-fifths of the globe 11. At its sides it supports the ciliary body 16 and the retina 18. A frontal saucer-shaped depression houses the lens.

The lens 21 of the eye is a transparent bi-convex body of crystalline appearance placed between the iris 17 and vitreous body 26. Its axial diameter varies markedly with accommodation. A ciliary zonule 27, consisting of transparent fibers passing between the ciliary body 16 and lens 21 serves to hold the lens 21 in position and enables the ciliary muscle to act on it.

Referring again to the cornea 12, this outermost fibrous transparent coating resembles a watch glass. Its curvature is somewhat greater than the rest of the globe and is ideally spherical in nature. However, often it is more curved in one meridian than another giving rise to astigmatism. A central third of the cornea is called the optical zone with a slight flattening taking place outwardly thereof as the cornea thickens towards its periphery. Most of the refraction of the eye takes place through the cornea.

Figure 2:
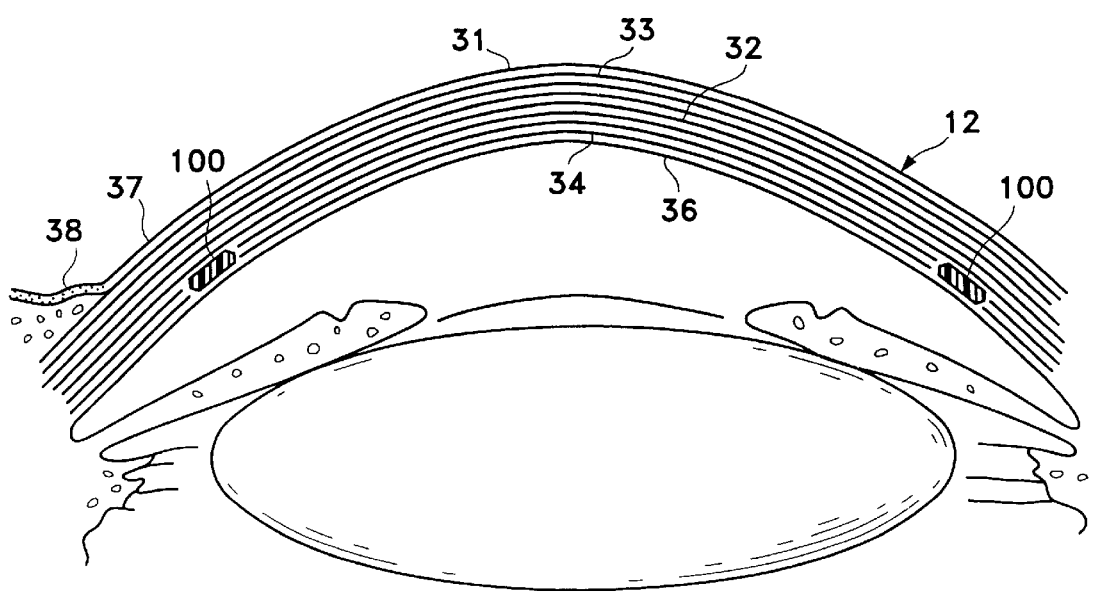
FIG. 2 is a drawing showing the horizontal section of the anterior portion of an eye.

Referring to FIG. 2, a more detailed drawing of the anterior portion of the globe, shows the various layers of the cornea 12, the outermost layer being the epithelium 31. Epithelial cells on the surface function to maintain transparency of the cornea 12. These epithelial cells are rich in glycogen, enzymes and acetylcholine and their activity regulates the corneal corpuscles and controls the transport of water and electrolytes through the lamellae of the stroma 32 of the cornea 12.

An anterior limiting lamina 33, referred to as Bowman's membrane or layer, is positioned between the epithelium 31 and the stroma 32 of the cornea. The stroma 32 is comprised of lamella having bands of fibrils parallel to each other and crossing the whole of the cornea. While most of the fibrous bands are parallel to the surface, some are oblique, especially anteriorly. A posterior limiting lamina 34 is referred to as Descemet's membrane. It is a strong membrane sharply defined from the stroma 32 and resistant to pathological processes of the cornea.

The endothelium 36 is the most posterior layer of the cornea and consists of a single layer of cells. The limbus 37 is the transition zone between the conjunctiva 38 and sclera 13 (See FIG. 1) on the one hand and the cornea 12 on the other.

The Method of the Invention

FIGS. 3–9 show the method for inserting a biocompatible material into the corneal stroma. In this case the biocompatible material is an intrastromal corneal ring (ICR). Other forms of biocompatible materials may be inserted into the corneal stroma, including but not limited to relatively stiff (high modulus of elasticity) physiologically acceptable polymers such as polymethylmethacrylate (PMMA), TEFLON, flourinated ethylene propylene (FEP), polycarbonate, polysulfones, epoxies, or polyolefins such as polyethylene, polypropylene, polybutylene, and their mixtures and interpolymers. By "high modulus of elasticity", is meant moduli greater than about 3.5 kpsi. Many of these polymers are known in the art to be appropriately used in hard contact lenses. Any polymer which is physiologically suitable for introduction into the body may useful in the inserts of this invention. Many of the listed polymers are known to be suitable as hard contact lenses. For instance, PMMA has a long history in ophthalmological usage and consequently is quite desirable for use in these inserts.

Additionally, the biocompatible material may be low modulus polymers, e.g., those having a modulus of elasticity below about 3.5 kpsi, more preferably between 1 psi and 1 kpsi, and most preferably between 1 psi and 500 psi, which are physiologically compatible with the eye. Most polymeric materials used in soft contact lenses are suitable as the biocompatible material of this invention. The class includes physiologically compatible elastomers and such crosslinked polymeric gels as polyhydroxyethylmethacrylate (Poly-HEMA) or polyvinylpyrrolidone (PVP), polyethylene oxide, or polyacrylates, polyacrylic acid and its derivatives, their copolymers and interpolymers, and the like as well as biologic polymers such as crosslinked dextran, crosslinked heparin, or hyaluronic acid.

In many instances, the biocompatible material may be hybrid, that is to say, it is made up of a number of polymeric layers typically with a soft or hydratable polymer on its outer surface. These hybrid materials may be partially hydrated or fully hydrated hydrophilic polymers that are typically slippery and consequently may contribute to the ease with which the insert may be introduced into the interlamellar tunnel. Suitable hydrophilic polymers include polyhydroxyethylmethacrylate (pHEMA), N-substituted acrylamides, polyvinylpyrrolidone (PVP), polyacrylamide, polyglycerylmethacrylate, polyethyleneoxide, polyvinyl alcohol, polyacrylic acid, polymethacrylic acid, poly (N, N-dimethyl amino propyl-$N^1$-acrylamide) and their copolymers and their combinations with hydrophilic and hydrophobic comonomers, crosslinks, and other modifiers. Thermoplastic hydrogels include hydropolyacrylonitrile, polyvinyl alcohol derivatives, hydrophilic polyurethanes, styrene-PVP block copolymers and the like.

Figure 3:
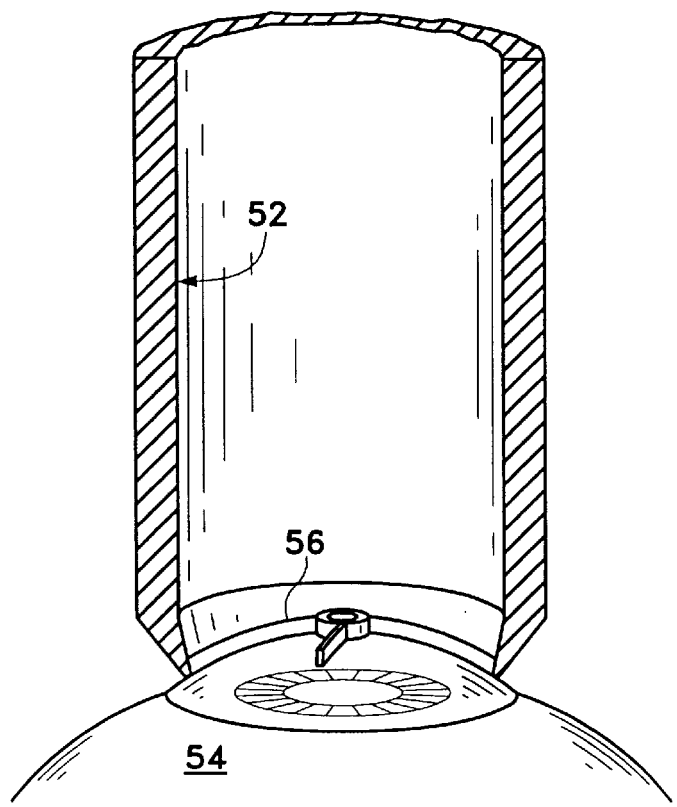
FIG. 3 is a front perspective view showing the radial incision marker and its relationship to the eye during use.

FIG. 3 shows a radial incision marker (52) placed on the front of a patients eye (54). The surgeon marks the center of the cornea with a blunt instrument using an operating microscope for fixation or another comparable fixation technique. The radial incision marker (52) with centering reticle (56) is placed on the cornea about the impression previously made. A light impression is made with the centering reticle to mark the position where the incision will be made.

The thickness of the cornea at the position of the proposed incision is determined using an ultrasonic pachymeter or other depth measuring device. The thickness is usually between about 0.65 and 0.75 mm. The incision will be made to a depth of about two-thirds of the thickness of the cornea or between about 0.40 and 0.50 mm, using the incision tool (66) shown in FIG. 4. The incision blade (68) on the incision tool (66) is set such that the blade (68) is between about 0.40 and 0.50 mm long, according to the measured thickness of the cornea. The incision blade (68) is then positioned at the previously marked position of the proposed incision and the incision is made. The incision extends through the epithelium and Bowman's membrane and is approximately 1–2 mm long and between about 0.40 and 0.50 mm deep. The incision is on a radius of the cornea. A small spatula which fits into the incision may be used to make an initial separation in the inner lamellar layers at the bottom of the incision within the stroma. This "teasing" of the lamella will facilitate the insertion of the depth measuring gauge (70) (see FIG. 5). A depth measuring gauge (70) (in this case, a gap gauge) is inserted into the incision to determine if the depth is, in actuality, as desired. If the gauge is easily inserted into the incision, the tissue is thinner than the gap and if it cannot be inserted, the tissue is thicker than the gap.

Figure 6:
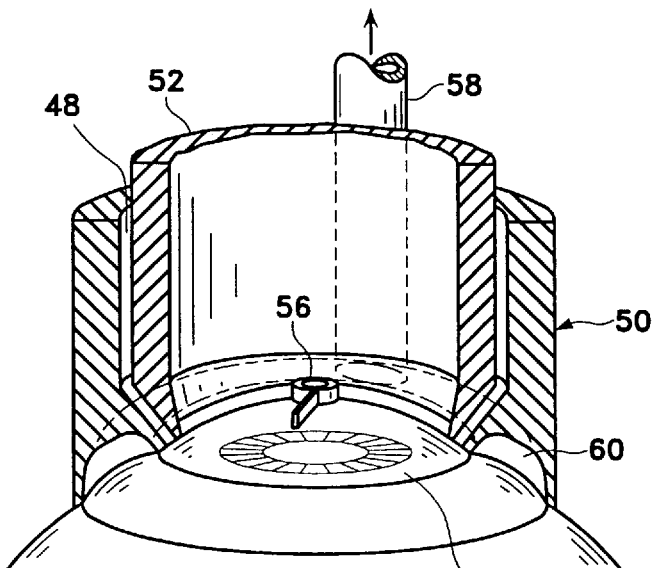
FIG. 6 is a front perspective view showing the application of vacuum to the circumcorneal vacuum ring.

Once it has been determined that the incision extends to the correct depth, as shown in FIG. 6 the radial incision marker (52) is placed inside the central bore (48) of the vacuum centering guide (50), and the combination is placed on the front of the patient's eye (54) using the centering reticle (56) on the radial incision marker (52) to center the vacuum centering guide (50) on the center mark previously made. At this point, vacuum is applied to the circumcorneal vacuum ring (60) on the vacuum centering guide (50) through a vacuum source line (58). The amount of vacuum applied is between about 10 and 27 mm Hg. The radial incision marker (52) is then removed from the vacuum centering guide (50). It may be observed that within the circumcorneal vacuum ring (60) there is a slight bulging of the eye. This bulging of the eye contacts the vanes within the vacuum chamber which helps prevent rotation or other movement of the vacuum guide (50).

Figure 7:
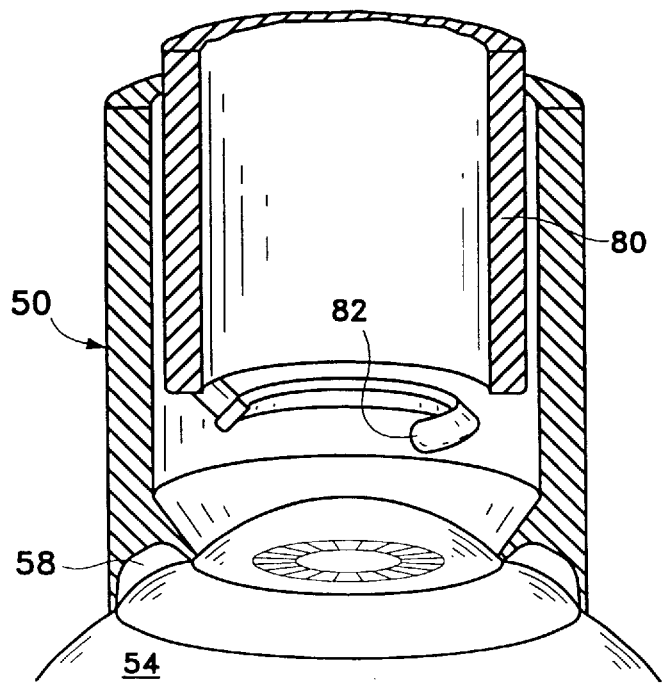
FIG. 7 is a front perspective view showing the insertion of a counter-clockwise dissector blade into the corneal stroma.

With the vacuum centering guide (50) firmly affixed to the eye, the counter-clockwise dissector barrel (80) is introduced into the central bore of the vacuum centering guide (50) (see FIG. 7). Alternatively, the procedure may begin with the clockwise dissector (86) shown in FIG. 8. For purposes of the following discussion, however, a procedure that begins with the counter-clockwise dissector will be described.

The counter-clockwise dissector blade (82) may form an arc of between 0° and 360°, preferably forms an arc of between about 170° and 240° and is shown in the drawings to form an arc of about 200°. The dissector blade (82) is introduced into the cornea through the incision in the cornea and rotated counter-clockwise in this case past the 180° point, through an arc of approximately 200°. The dissector blade (82) is then rotated clockwise and the blade is backed out of the inner subsurface lamellar tunnel it has formed.

Figure 8:
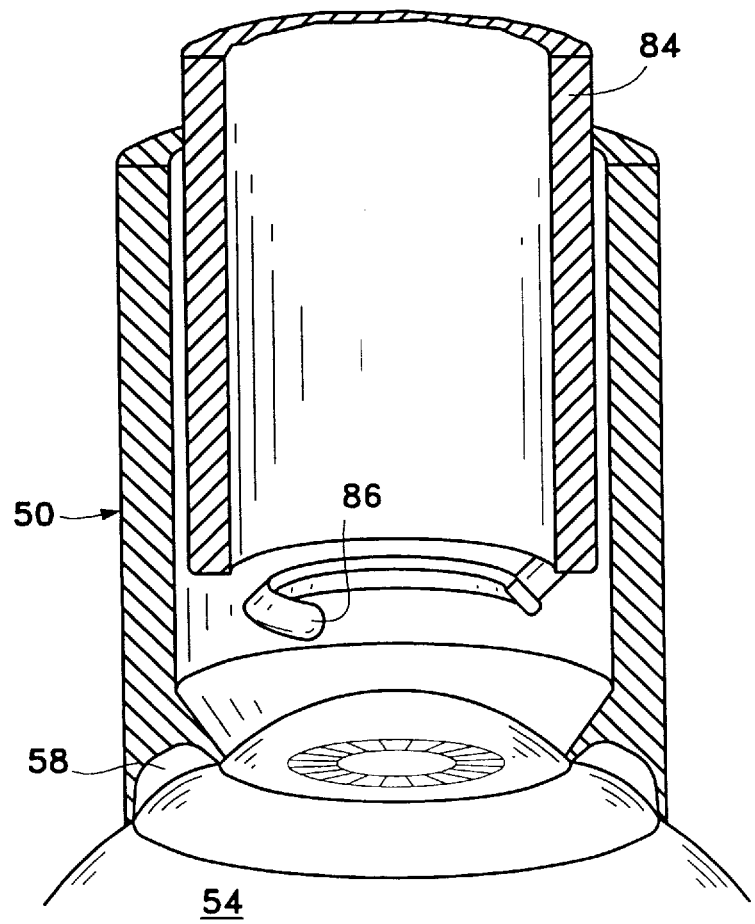
FIG. 8 is a front perspective view showing the insertion of a clockwise dissector blade into the corneal stroma.
Figure 9A:
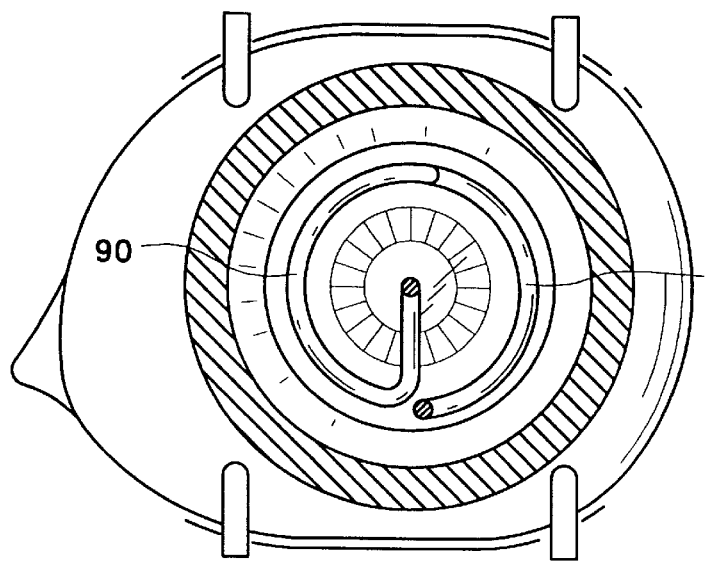
FIG. 9A shows a top view and FIG. 9B shows a side view of the insertion of clockwise and counter-clockwise probes.
Figure 9B:
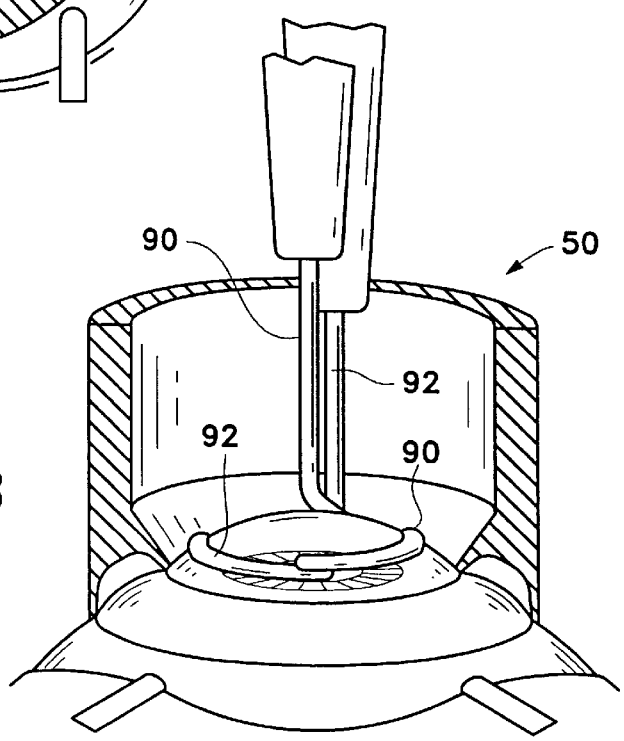
Figure 10:
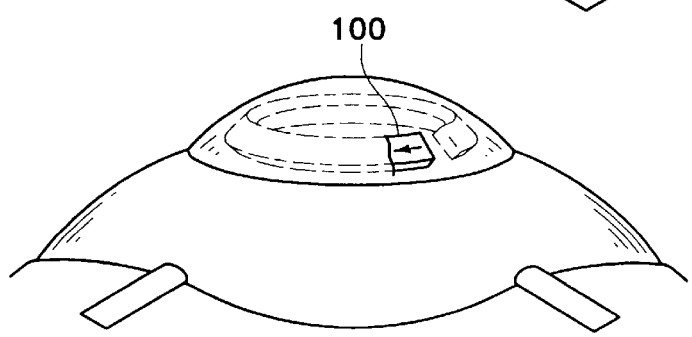
FIG. 10 is a front perspective view showing the insertion of the ICR in the intrastromal channel.

Next, the clockwise dissector barrel (84) is introduced into the support base (see FIG. 8). The dissector blade (86) is introduced into the cornea through the incision in the cornea and rotated clockwise in this case past the 180° point, through an arc of approximately 200°. If the channels connect, there will be an abrupt decrease in resistance to continued dissection. If this occurs, the dissector blade is rotated counter-clockwise, the blade is backed out of the inner subsurface lamellar tunnel it has formed and the biocompatible material in this case, the ICR (100) will be inserted through the original incision and into the channel. (See FIG. 10 and also FIG. 2.)

If decrease in resistance to continued dissection is not felt, a clockwise probe (90) (see FIG. 9A) is inserted into the clockwise channel. If breakthrough occurred, the probe tip will easily rotate past 200° clockwise rotation. Optimally, the probe will rotate past 200° and clearly into the channel created by the counter-clockwise dissector. The probe can then be withdrawn, the vacuum eased so that the vacuum centering guide can be removed, and the biocompatible material, in this case the ICR, inserted. If, however, the probe does not touch rotate past 200°, it will be possible to determine which channel, the clockwise or the counter-clockwise channel is the lower channel. The clockwise and counter-clockwise probes (90 and 92 respectively) are inserted into the clockwise and counter-clockwise channels, respectively (see FIGS. 9A and B). The lower channel is determined by observing the position of the probes at the point where their tips overlap. Once this has been determined, the probes are removed from the channels by rotating them clockwise for the counter-clockwise probe and counter-clockwise for the clockwise probe.

If it has been determined that the clockwise channel is the lower one, a clockwise channel connector with an arc of between about 0° and 360°, preferably of between about 240° and 360° and in FIGS. 17A and B shown to be about 330° is inserted clockwise into the clockwise channel and rotated clockwise in a similar manner as shown in FIG. 8 until it is observed to breakthrough into the counter-clockwise channel or until it has rotated 330°. If the channels are connected, there will have been an abrupt decrease in resistance to continued dissection. If this is the case, the clockwise channel connector is then rotated counter-clockwise and removed from the clockwise channel. The vacuum is then eased and the vacuum centering guide (50) shown in FIG. 6 is removed. The biocompatible material, in this case the ICR, can be inserted. If the channels do not meet, a clockwise finish channel connector with an arc of between about 360° and 510°, preferably between about 380° and 450° and in FIGS. 19A and B shown to be about 400° will be inserted into the lower, clockwise channel and rotated clockwise in a similar fashion as shown in FIG. 8 until the lower channel connects with the upper channel, or until the finish channel connector tip rotates through to the entry incision. Channel connecting may be determined when an abrupt decrease in resistance to continued dissection is observed. Once the clockwise and counter-clockwise channels have been connected, the finish channel connector is removed and the vacuum is eased. The vacuum centering guide (50) shown in FIG. 6 can then be removed from the eye and the biocompatible material inserted.

If it has been determined that the counter-clockwise channel is the lower one, a counter-clockwise channel connector with an arc of between about 0° and 360°, preferably of between about 240° and 360° and in FIGS. 18A and B shown to be about 330° is inserted counter-clockwise into the counter-clockwise channel and rotated counter-clockwise in a similar fashion as shown in FIG. 7 until it is observed to breakthrough into the clockwise channel or until it has rotated 330°. If the channels are connected, there will have been an abrupt decrease in resistance to continued dissection. If this is the case, the counter-clockwise channel connector is then rotated clockwise and removed from the counter-clockwise channel. The vacuum is eased and the vacuum centering guide (50) shown in FIG. 6 can then be removed from the eye. The biocompatible material, in this case the ICR, can now be inserted.

Figure 19A:
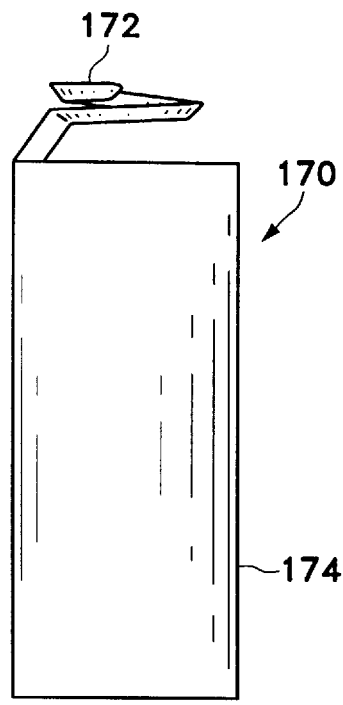
FIG. 19A is a side view and FIG. 19B is a bottom view showing the clockwise finish channel connector.

If the channels do not meet, a counter-clockwise finish channel connector with an arc of between about 360° and 510°, preferably between about 380° and 450° and in FIGS. 19A and B shown to be about 400° will be inserted into the lower, counter-clockwise channel and rotated counter-clockwise in the manner shown in FIG. 7 until the lower channel connects with the upper channel, that is there is an abrupt decrease in resistance to continued dissection or until the finish channel connector tip rotates through to the entry incision. Once the clockwise and counter-clockwise channels have been connected, the finish channel connector is removed. The vacuum is eased on the vacuum centering guide (50) and it is removed from the eye. Next, the biocompatible material, in this case the ICR (100) may be introduced into the intrastromal channel in the clockwise direction or, in the direction of the channel connector if one was used. The ends of the ICR, may be joined using techniques described in the patents discussed above.

The Devices of the Invention

FIGS. 4, 5 and 11–20 show the devices useful in the method of the invention.

Figure 4:
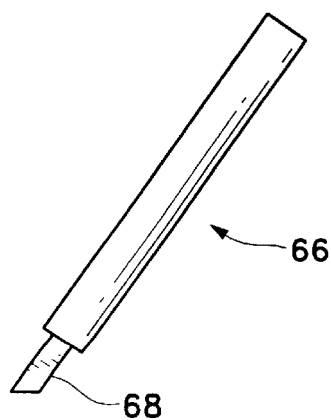
FIG. 4 is a side view showing the incision blade.
Figure 5:
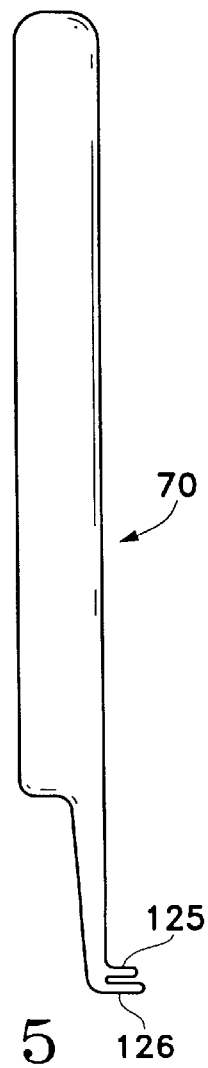
FIG. 5 is a side view showing the gap gauge.

The incision for insertion of the dissector blades is made with the incision tool (66) shown in FIG. 4. The incision blade (68) is of a size and configuration that allows the blade (68) to enter the cornea at a depth and angle suitable for cutting a precise depth into the corneal stroma. After the initial incision is complete, a small spatula may be inserted into the incision to separate the lamellar layers at both sides of the bottom of the incision. The lower fork (126) of the gap gauge (70) shown in FIG. 5 is then inserted down into the lamellar separation. The gap gauge (70) has upper and lower forks (125 and 126 respectively), the distance from the bottom edge of the upper fork to the top edge of the lower fork (the gap) being from about 0.375 to 0.525 mm. The lower fork (126) will be placed into the lamellar separation to determine the separation depth. If the corneal tissue is easily inserted into the gap between the upper and lower forks, the tissue is thinner than the gap and a deeper incision may be required. If the corneal tissue cannot be easily inserted into the gap, the tissue is thicker than the gap.

Figure 11A:
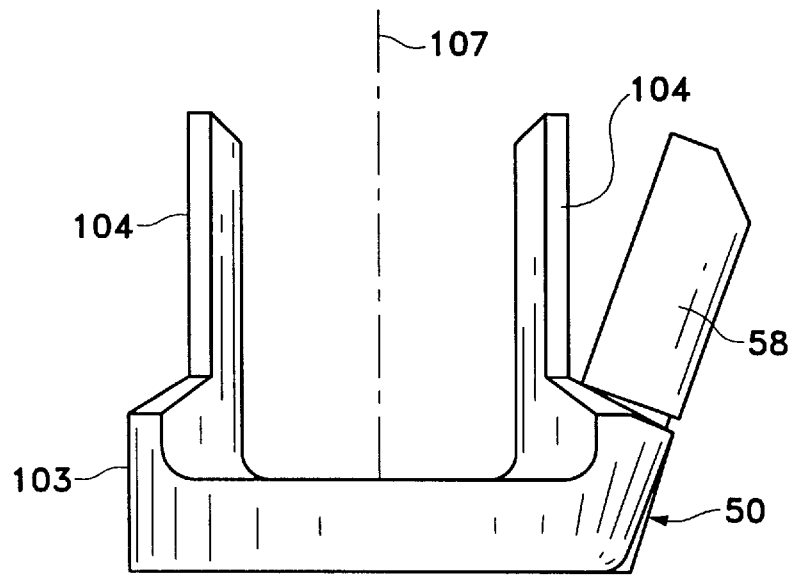
FIG. 11A is a side view and FIG. 11B is a bottom view showing the vacuum guide.
Figure 11B:
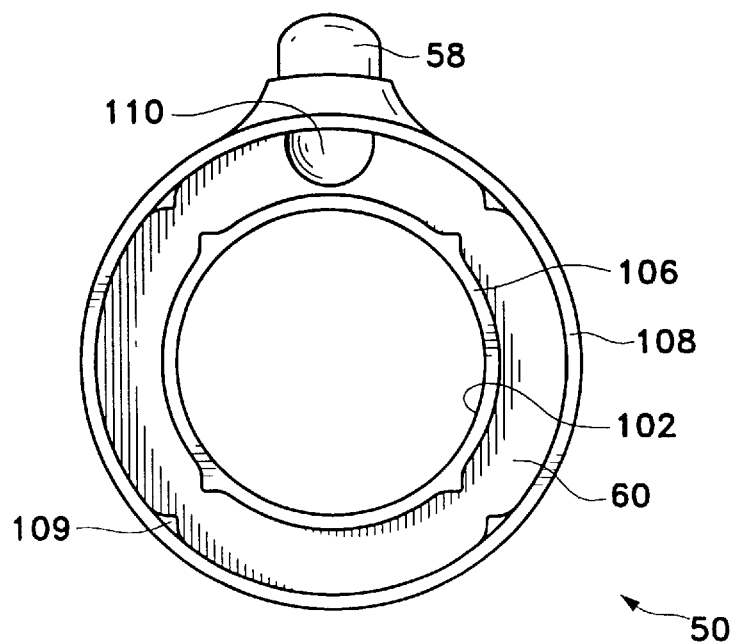

FIGS. 11A and B show the vacuum guide (50). The vacuum centering guide (50) includes an annular circumcorneal vacuum ring (60) at the end proximal the cornea and a cylindrical or central bore (102) extending from the end of the vacuum guide distal the eye (54). The vacuum guide (50) typically contains a solid ring (103) that extends vertically approximately the distance of one half of the diameter of the vacuum centering guide (50). Wall portions (104) extend vertically from the solid ring (103) and support the other devices inserted into the central bore (102) while allowing for excellent view of those devices and the eye. The vacuum is brought in from vacuum source line (58). The circumcorneal vacuum ring (60) is configured so that it meets with and seals to the front of the eye rendering the vacuum guide (50) relatively immobile when the support base is applied to the front of the eye and a suitable vacuum is applied to the vacuum source line (58). The vacuum chamber forms an annular vacuum space against the front of the eye. The circumcorneal vacuum ring (60) is made up of an inner wall (106) terminating on its inside by the central bore (102). The central bore (102) is at least large enough to see the entirety of the dissector blade (i.e. 131 in FIG. 13A) as is discussed below. The central bore (102) has an axis (107) which substantially coincides with the axis of the dissector blade. The outer vacuum ring wall (108) desirably forms the outside of the vacuum centering guide (50). Interior to the circumcorneal vacuum ring (60) may be one or more ridges (109) which extend down to the corneal surface when the support base is attached to the guide. The ridges are positioned within the circumcorneal vacuum ring (60) to prevent rotation of the vacuum guide (50) during any surgical operation. The opening (110) to the vacuum source line (58) is shown in FIG. 11B.

Figure 12A:
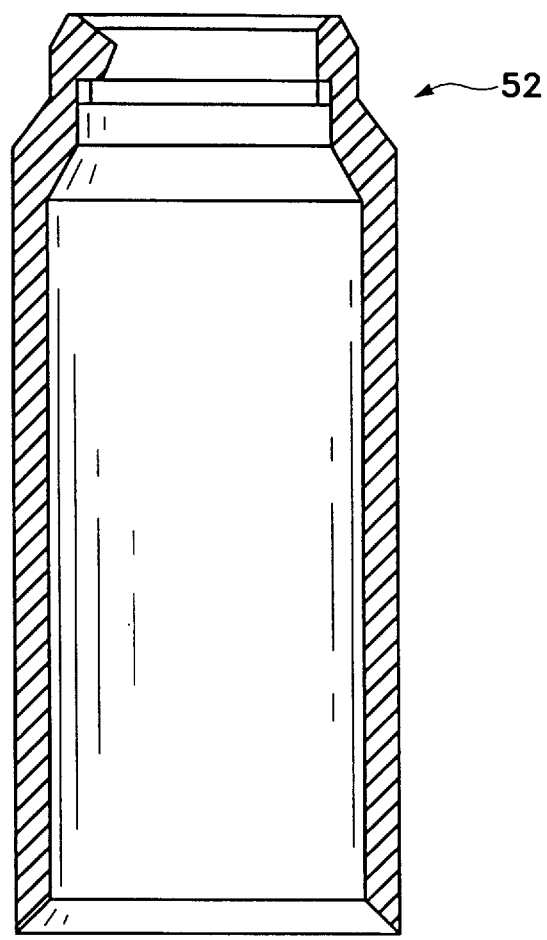
FIG. 12A is a side view and FIG. 12B is a bottom view showing the radial incision marker.
Figure 12B:
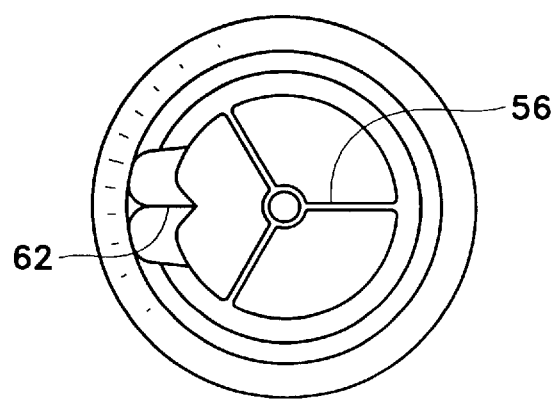

FIG. 12A shows a side view and FIG. 12B shows a bottom view of the radial incision marker (52). The sighting portion (56) on the inside bore of the radial incision marker (52) allows for making a marking on the cornea at the site of the proposed incision with the incision marker blade (62). Further, the radial incision marker (52) is used to center the vacuum centering guide one the eye. The radial incision marker fits into the central bore (102) of the vacuum guide (50). Once the surgeon determines that the vacuum guide (50) is properly centered by using the radial incision marker (52), vacuum is applied through the vacuum source line (58) on the vacuum guide (50) and its terminal opening (110) in the circumcorneal vacuum ring (60) (see FIGS. 11A and B).

Figure 13A:
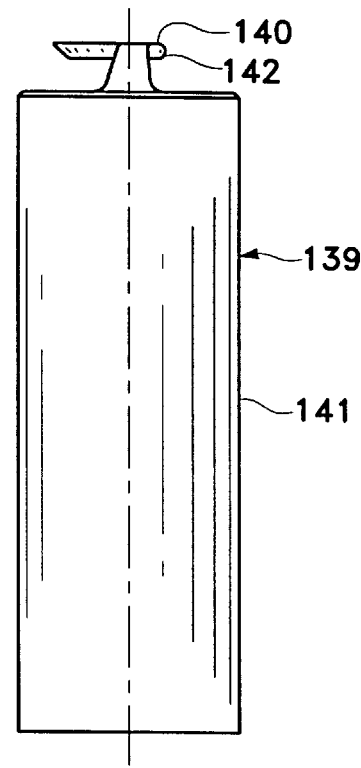
FIG. 13A and C are side views and FIG. 13B is a top view showing the counter-clockwise dissector.

Once the vacuum guide (50) is affixed to the front of the eye, the radial incision marker (52) is removed from the center bore (102) of the vacuum guide (50) and the counter-clockwise dissector barrel (130) is inserted into the central bore (102) of the vacuum guide (50) (see FIGS. 13A and B.) The dissector blade (131) is attached to the dissector barrel (130) by the dissector blade support arm (132). As the barrel (130) rotates, it defines a barrel axis. The barrel axis (133) is coincident to the blade axis (134) discussed below.

Figure 13B:
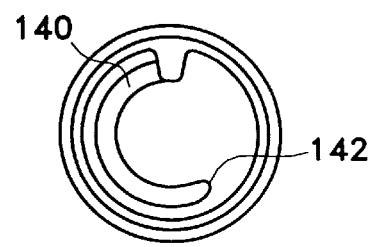

FIG. 13A is a side view and FIG. 13B is a bottom view of the counter-clockwise dissector (129). The blade (131), in cross-section, is desirably rectangular (see FIG. 13D). This permits a large amount of material to be incorporated in the blade and yet form a substantially rectangular path in the interlamellar spaces of the corneal stroma. The blade (131) is in the shape of a major arc of between about 0° and 360°, preferably between about 170° and 240°, and shown to be about 200° having its center the axis (134) as shown in FIG. 13B. The blade's major arc is in a plane perpendicular to that axis (134).

Figure 13C:
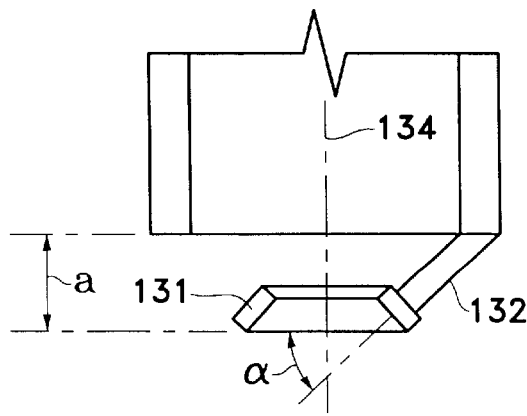
FIG. 13D is a side cross-section view of the counter-clockwise dissector.

The dissector blade (131) is formed so that the dissector blade support arm (132) is at an angle α of up to about 90° (see FIG. 13C). The angle of the blade support arm (132) to the plane of the blade (131) may be a value of 0° to 90°. It is preferably between 0° and 80°, more preferably the angle is between 10° and 50° and most preferably about 34° (±5°) to the plane of the dissector blade. This angle results in the dissector blade support arm (132) being generally perpendicular to the cornea when it is inserted into the incision provided for introduction of the dissector blade (131) into the corneal stroma. This angle, although not absolutely critical, is desirable and has been found to prevent tearing of the epithelium during the corneal operation. The length of blade angle support arm (132) is sufficient that the entire dissector blade (131) is visible through the top of the dissector barrel during use. The outer diameter of the dissector barrel (130) is slightly less than the diameter of the bore (102) of the vacuum guide (50), thus allowing for rotation of the dissector barrel (130) within the vacuum guide (50). The overall relationship of the sizes of the diameter of the arc of the blade (131) to the length of the dissector barrel is desirably chosen so that the ratio of the length to the arc diameter is between 0.25:1 and 15:1; specifically between 0.4:1 and 1:1, at least about 1:1 and less than about 3:1; and at least about 3:1 but less than 15:1. Again, these ratios allow ease of manipulation by the surgeon.

The dissector blade (131) has two other physical parameters that are believed to be important to the effective operation of the vacuum guide (50) in providing an inter-lamellar channel in the corneal stroma. Upon rotation of the dissector barrel (130), the dissector blade (131) must move in a path which is substantially planar. That is to say, the path of the dissector blade (131), as it moves in the corneal intrastromal lamellar space described above, must not vary either up or down during the dissector barrel (130) rotation. The distance "a" shown in FIG. 13C is a constant. The blade (131) can be considered to be in a plane which is perpendicular to the axis (134) which is in the center of the dissector blade (131).

Figure 13D:
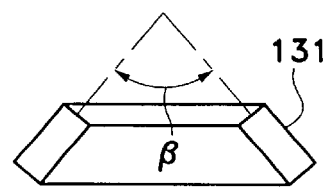

Similarly, the cone angle β shown in FIG. 13D is preferably 112° (±30°). Again, this permits the dissector blade (131) to produce a channel which is parallel to the lamella found in the corneal stroma. The cone angle β may, of course, vary a few degrees dependent on such variables as the geometry of the ICR installed, the size of the eye.

The dissector blade (131) may be made of a variety of materials including but not limited to metals such as stainless steel and other similarly strong and biocompatible materials; and may be coated with a lubricous material such as, but not limited to polyHEMA hydrogel, cross-linked collagen, cross-linked hyaluronic acid, siloxane gels, polyvinyl pyrrolidone, TEFLON, FEP and organic-siloxane gels.

The dissector barrel (130) having dissector blade (131) on its lower end is introduced into the inner bore of the vacuum guide (50). The leading edge of the dissector blade which blade may be rounded and blunt so as not to tear corneal tissue is introduced into the incision made by the incision blade and the dissector blade is rotated clockwise as shown. The dissector barrel is rotated between about 170° and 240°, in this case 200° clockwise in order to make a 200° channel. The dissector barrel is then rotated counter-clockwise and removed.

Figure 14A:
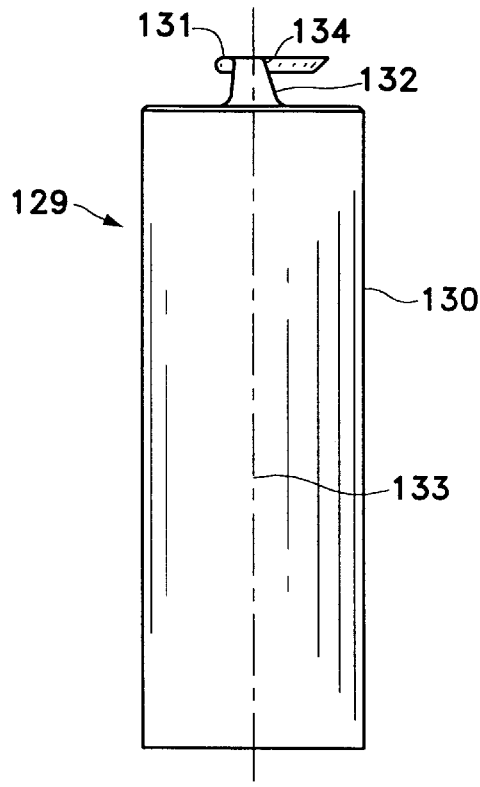
FIG. 14A is a side view and FIG. 14B is a top view showing the clockwise dissector.
Figure 14B:
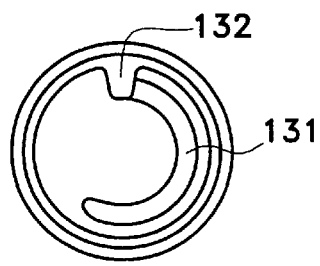

FIGS. 14A and 14B show a side view and bottom view of the clockwise dissector (139). As is shown, the dissector (139) is constructed as described above with regard to FIG. 13 A–D but the dissector blade (140) is in a clockwise rather than a counter-clockwise configuration. Following making the 200° counter-clockwise channel described above, the dissector barrel (141) having dissector blade (140) on its lower end is introduced into the inner bore of the vacuum guide (50). The leading edge (142) of the dissector blade (140) is introduced into the incision made by the incision blade and the dissector barrel (141) is rotated between about 170° and 240°, in this case 200° clockwise in order to make a 200° channel. The dissector barrel (141) is then rotated counter-clockwise and removed. It is of course possible to make the clockwise channel before making the counter-clockwise channel in a similar manner to what has been described above.

FIGS. 15A and B show side and bottom views of clockwise probe (90) and FIG. 16A and B show side and bottom views of the counter-clockwise probe (92). The probes are designed such that the axes of the handles (151 and 152) are on the diameter of the portion of the probes (153 and 154) that are inserted into the clockwise and counter-clockwise channels of the eye. The clockwise probe (90) is designed with a support arm (155) that has an angle a as shown in FIG. 15A or as described above with respect to the dissector blade. The counter-clockwise probe (92) has a support arm (156) that is vertical as shown in FIG. 16A. The arc of the probes may be between 0° and 360°, preferably between about 180° and 360°, and is shown in the drawings to be about 200°.

FIGS. 17A and B show bottom and side views, respectively of the clockwise channel connector (160), and FIGS. 18A and B show bottom and side views, respectively, of the counter-clockwise channel connector (161). The blades (162 and 163) and barrels (164 and 165) of the channel connectors are as described above with respect to the dissectors, except that the arcs of the blades are between about 0° and 450°, preferably between about 240° and 400°, and in FIGS. 17A and B and 18A and B shown to be about 330°.

Figure 20A:
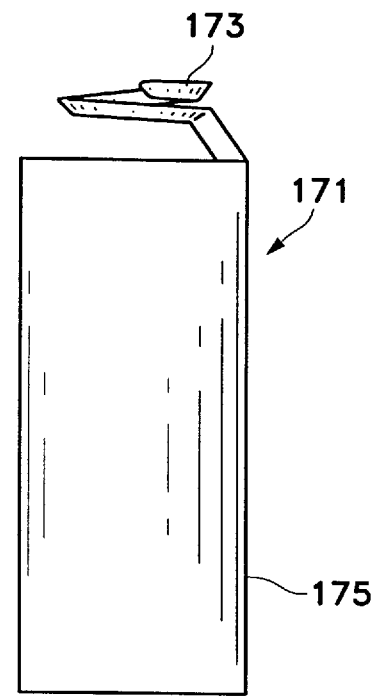
FIG. 20A is a side view and FIG. 20B is a bottom view showing the counter-clockwise finish channel connector.
Figure 19B:
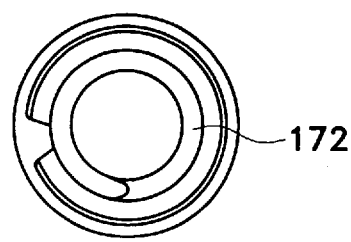
Figure 20B:
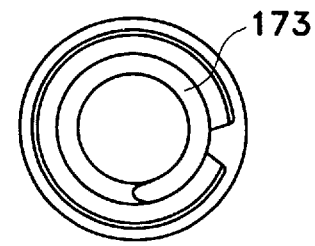

FIGS. 19A and B show bottom and side views, respectively of the clockwise finish channel connector (170), and FIGS. 20A and B show bottom and side views, respectively of the counter-clockwise finish channel connector (171). The blades (172 and 173) and barrels (174 and 175) of the finish channel connectors are as described above with respect to the dissectors, except that the arcs of the blades are spirals of between about 360° and 510°, preferably between about 380° and 450° and shown in the drawings to be about 420°.

This invention has been described and exemplified in some detail. Those having ordinary skill in this art would recognize variations and equivalents which would be well within the scope of the invention disclosed herein but perhaps outside the scope of the appended claims. It is applicants' intention that these equivalent variations be included within the scope of this invention.

We claim:

1. A depth measuring gauge for use in determining the depth of an incision formed in a cornea, said gauge comprising:

(a) an upper fork with a lower edge;

(b) a lower fork with an upper edge and a lower edge;

(c) said upper and lower forks being arranged to form a gap between said upper edge of said lower fork and said lower edge of said upper fork, wherein the ease of insertion of corneal tissue into the gap facilitates determining whether the thickness of the corneal tissue being inserted into the gap and measured by the gauge is greater or less than the width of said gap, measured as the distance between said upper fork lower edge and said lower fork upper edge.

2. The depth measuring gauge of claim 1, wherein said gap is sized to receive a portion of a human cornea to indicate the thickness of said portion.

3. The depth measuring gauge of claim 1, wherein the width of said gap is from about 0.375 mm to about 0.525 mm.

4. The depth measuring gauge of claim 1, wherein said upper edge of said lower fork and said lower edge of said upper fork are substantially parallel.

5. The depth measuring gauge of claim 1, wherein said lower fork is adapted for insertion into a lamellar separation in the cornea.

* * * * *